(12) United States Patent
Bunzel et al.

(10) Patent No.: US 6,710,153 B2
(45) Date of Patent: Mar. 23, 2004

(54) METHOD FOR PRODUCING PHOSPHONIUM PHENOLATES

(75) Inventors: Lothar Bunzel, Kempen (DE); Uwe Hucks, Alpen (DE); Annett König, Leverkusen (DE); Silke Kratschmer, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/168,166

(22) PCT Filed: Dec. 7, 2000

(86) PCT No.: PCT/EP00/12325

§ 371 (c)(1), (2), (4) Date: Jun. 17, 2002

(87) PCT Pub. No.: WO01/46100

PCT Pub. Date: Jun. 28, 2001

(65) Prior Publication Data

US 2003/0013837 A1 Jan. 16, 2003

(30) Foreign Application Priority Data

Dec. 20, 1999 (DE) .......................................... 199 61 520

(51) Int. Cl.$^7$ ................................................ C08G 64/00
(52) U.S. Cl. ........................... 528/196; 502/150; 568/9; 568/11; 528/198
(58) Field of Search .......................... 502/150; 528/196, 528/198; 568/9, 11

(56) References Cited

U.S. PATENT DOCUMENTS 6,476,273 B2 * 11/2002 Konig et al. ................... 568/11
2001/0005765 A1   6/2001 Konig et al. ................... 568/11

FOREIGN PATENT DOCUMENTS

| EP | 826 693 | 3/1998 |
| WO | 99/00395 | 1/1999 |

* cited by examiner

Primary Examiner—Terressa Boykin
(74) Attorney, Agent, or Firm—Joseph C. Gil; Aron Preis; Gary F. Matz

(57) ABSTRACT

A process for the production of phosphonium phenolates is disclosed. The process entails reacting a phosphonium halide and phenol in an aqueous alkaline solution. The phosphonium phenolate produced is separated from the synthesis mixture by crystallization

12 Claims, No Drawings

METHOD FOR PRODUCING PHOSPHONIUM PHENOLATES

This application relates to a process for the production of phosphonium phenolates.

The production of phosphonium phenolates has already been described in DE-A-197 273 51. However, the phosphonium phenolates produced in this manner contain impurities which are disadvantageous for subsequent use. It is thus known that phosphonium phenolates may be used as transesterification catalysts for melt transesterification. Purity is, however, of vital significance for this application as impurities may result in discolouration, variations in activity or secondary reactions in the transesterification process. Moreover, this process generates a considerable quantity of solvent as waste product, which entails elevated disposal costs. The product is furthermore exposed to elevated temperatures during removal of residual solvent. Since phosphonium phenolates readily form addition products with phenol, exposure to elevated temperatures should be kept as slight as possible.

The object of the present application is accordingly to provide a process in which exposure to elevated temperatures and the quantity of solvent generated remain as slight as possible, but in which the purity of the phosphonium phenolate is as high as possible.

The application provides a process for the production of phosphonium phenolates by reacting phosphonium halides and phenols in an aqueous alkaline solution, which is characterised in that the phosphonium phenolate produced is separated from the synthesis mixture by crystallisation.

The reaction is preferably performed at temperatures of 0 to 55° C., in particular of 15 to 50° C.

The reaction is preferably performed at molar ratios of phenol to phosphonium halide of 2:1 to 10:1, preferably of 4.5:1 to 6:1 and in particular of 5:1.

The reaction is preferably performed at pH values of 9.5 to 11, preferably of 9.5 to 10.5 and in particular of 10 to 10.5.

The reaction is optionally performed in the presence of alcohols in quantities of 50 wt. % to 200 wt. %, preferably of 66 wt. % to 125 wt. %, relative to the quantity by weight of the aqueous phase, wherein the alcohols preferably have a solubility in pure water of at most 15 wt. %.

The phosphonium phenolates produced in this manner contain no more than 0.1 wt. % of halide.

Phosphonium halides of the formula (I) are in particular used for the reaction

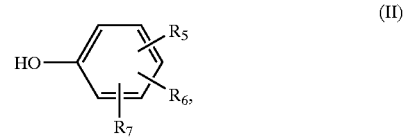

in which
R$_1$ to R$_4$ identical or different, each denote a C$_1$–C$_{12}$ alkyl, C$_5$–C$_6$ cycloalkyl, C$_7$–C$_{12}$ aralkyl or C$_6$–C$_{14}$ aryl residue and
X$^{(-)}$ denotes a halide ion, preferably F$^{(-)}$, Cl$^{(-)}$ or Br$^{(-)}$ and
n denotes the number 1 or 2, wherein, when n=2, R$_4$ denotes a C$_2$–C$_{12}$ alkylene residue.

Residues R$_1$ to R$_4$ are preferably identical or different and each denote a C$_6$–C$_{14}$ aryl residue or the residues R$_1$ to R$_3$ each denote a C$_6$–C$_{14}$ aryl residue and R$_4$ denotes a C$_2$–C$_{12}$ alkylene residue.

Such phosphonium halides and the production thereof are known or are obtainable using known methods (c.f. for example Houben-Weyl, *Methoden der organischen Chemie*, volume XII/1, pages 79 et seq. and Worrall, *J. Amer. Chem. Soc.* 52 (1930), pages 293 et seq.).

These compounds (I) are formed on the reaction of trialkyl- or triarylphosphines, for example of triphenylphosphine, with haloarylene or haloalkylene, for example benzyl bromide, in the presence of metal salts (Friedel-Crafts alkylation) or in the presence of Grignard compounds and cobalt(II) chloride.

Phenols which are preferred for the reaction are phenol or substituted phenols as well as bisphenols.

Particularly preferred phenols are those of the formula (II)

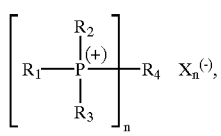

in which
R$_5$ to R$_7$ mutually independently denote H, C$_1$–C$_{12}$ alkyl, C$_5$–C$_6$ cycloalkyl, C$_7$–C$_{12}$ arylalkyl and C$_6$–C$_{14}$ aryl;
R$_5$ to R$_7$ preferably denote hydrogen.

Such phenols are known from the literature.

Phosphonium phenolates of the formula (III) are preferably produced

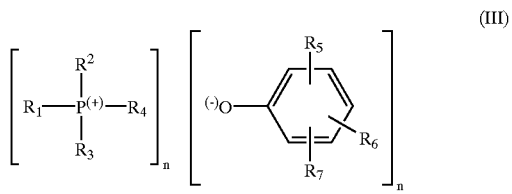

in which the residues R$_1$ to R$_7$ and n have the above-stated meanings.

Completely deionised water or distilled water is preferably used to produce the aqueous alkaline phase.

The pH value of 9.5 to 11.0, preferably of 9.5 to 10.5, particularly preferably of 10.0 to 10.5 is preferably established using an alkali metal hydroxide solution, preferably sodium hydroxide solution or potassium hydroxide solution, while taking the buffering action of phenol/Na phenolate into account.

The process according to the invention may be performed continuously or discontinuously, wherein discontinuous operation is preferred.

According to a preferred method, phenol, phosphonium halide and alcohol are initially introduced as a solution and water is added. The pH value is adjusted, optionally with cooling, to values 9.5 to 11.0, preferably of 9.5 to 10.5, particularly preferably of 10.0 to 10.5 by addition of alkali metal hydroxide solution. The temperature of 0 to 55° C., preferably of 15 to 50° C. is maintained during this operation, preferably by vigorous stirring of the reaction components. The duration of the reaction should be less than 2 hours, preferably less than 1 hour.

The phosphonium phenolate produced according to the invention is isolated, preferably by separating the aqueous phase from the organic phase using an alcohol which is sparingly soluble in water (the solubility of alcohols in water is known from the literature) and extracting the organic phase at least once, preferably three times with completely deionised water or distilled water. The solution is then cooled to 26 to 0° C., preferably to 23 to 10° C. The precipitated phenolate is then separated by suction filtration and purified by washing. The resultant product is optionally recrystallised and dried.

Alcohols suitable according to the invention for the reaction solution are aliphatic alcohols of the formula $C_nH_{2n+1}$—OH, in which n is an integer from 4 to 10 inclusive, such as for example n-butanol, isobutanol, n-pentanol, methylbutanols, neopentanol, amyl alcohols, branched and unbranched hexanols, heptanols, octanols, nonanols or decanols.

Alcohols suitable according to the invention for the reaction solution are also cycloaliphatic alcohols of the formula $C_nH_{2n-1}$—OH, in which n is an integer from 5 to 10 inclusive, such as for example cyclopentanol, methylcyclopentanols, cyclopentanemethanol, cyclopentylpropanols, cyclohexanol, cyclohexylethanols, cyclohexylpropanols, cyclohexylbutanols, methyl-, ethyl-, propyl- and butylhexanols, cycloheptanols, cyclooctanols.

Apart from completely deionised water, alcohols may also be used for washing the phenolate. In this case, apart from those for the reaction solution, water-soluble alcohols may also be used, such as for example ethanol, n-propanol or isopropanol. Propanols, in particular isopropanol, are preferred in this case.

Polyhydric aliphatic or cycloaliphatic alcohols may also be used according to the invention.

Preferred aliphatic alcohols are propanols, (iso)butanols, pentanols and hexanols, in particular isobutanol and isopropanol.

Preferred cycloaliphatic alcohols are cyclopentanol, cycloheptanol and cyclooctanol, particularly preferably cyclohexanol.

The weight ratio of water to alcohol is between 2:1 and 1:2, preferably between 1:1 and 1:2.

The alcohols to be used according to the invention are added to improve working up, as the phenol/alcohol mixture has a lower density than the aqueous solution and the organic phase is thus above the aqueous phase. The aqueous phase may thus be drained off from beneath, the organic phase, which contains the phenolate, may be washed with completely deionised water in the same separating vessel and the washing water again drained off from beneath.

If the alcohol is not added, only the aqueous saline solution is heavier than the organic phase and may be drained off from beneath. Phase inversion occurs on further washing with completely deionised water, the organic phase is heavier and thus beneath the aqueous phase. This working up method is more elaborate because a second working up vessel is required.

Quaternary phosphonium phenolates produced according to the invention are in particular compounds of the formulae (IV)

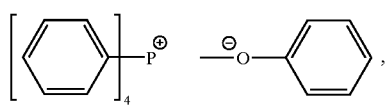

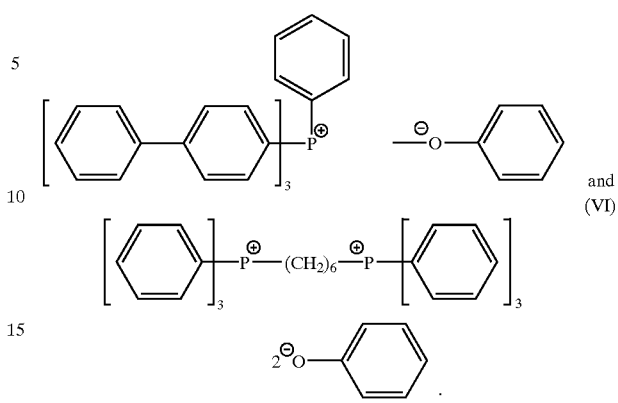

Using the process according to the invention, it is possible to produce phosphonium phenolates in elevated yields and at high purity.

The phosphonium phenolates produced in this manner are suitable in particular as catalysts for esterification and transesterification, in particular for the production of polycarbonates by the melt transesterification process (c.f. U.S. Pat. No. 3,442,854).

As is known, the melt transesterification process starts, for example, from aromatic diphenols, carbonic acid diaryl esters and optionally branching agents and/or monophenols.

The phosphonium phenolates obtainable according to the invention are used as catalysts in this case in quantities of $10^{-1}$ mol to $10^{-8}$ mol, preferably in quantities of $10^{-3}$ mol to $10^{-7}$ mol, per mol of diphenol.

Further details of the melt transesterification process are described in the literature (c.f. Hermann Schnell, *Chemistry and Physics of Polycarbonates, Polymer Reviews*, volume 9, 1964, pages 44 to 51, DE-A-1 031 512, U.S. Pat. Nos. 3,022,272, 5,340,905 and 5,399,659).

The thermoplastic polycarbonates produced with the phosphonium phenolates obtainable according to the invention are solvent-free, have a light inherent colour and are largely free of unwanted defects in the polycarbonate.

The polycarbonates produced in this manner may be used industrially in the form of the most varied mouldings in any applications in which thermoplastic polycarbonates have hitherto been used, such as in electrical engineering, as lamp covers, as safety screens or as optical data storage media, such as CD material.

EXAMPLES

Comparative Example 1

376 g (4.0 mol) of phenol, 800 ml of completely deioinsed water, 335.44 g (0.8 mol) of tetraphenylphosphonium bromide and 640 g of isobutanol are initially introduced into a 2 L round-bottomed flask equipped with a stirrer, thermometer and dropping funnel and are stirred at 20° C. to 25° C. 79 g (0.97 mol) of 49% sodium hydroxide solution are added dropwise within approx. 5 minutes, the pH value is checked with a glass electrode—it must be within a range from 9.5 to 11.0. The mixture is then stirred for 0.5 h at 45° C. After phase separation, the lower aqueous phase is drained off and the organic phase is washed three times with completely deionised water, it being possible in each case to drain off the washing water, as the heavier phase, from beneath. The isobutanol is then removed by distillation under a water-jet vacuum at 50° C.

The crystalline residue is dried under a vacuum at 100° C. The yield, determined using the P-NMR method, is 98.2% of the theoretical yield.

The results are shown in Table 1.

Example 1

376 g (4.0 mol) of phenol, 800 ml of completely deionised water, 335.44 g (0.8 mol) of tetraphenylphosphonium bromide and 640 g of isobutanol are initially introduced into a 2 L round-bottomed flask equipped with a stirrer, thermometer and dropping funnel and are stirred at 20° C. to 25° C. 79 g (0.97 mol) of 49% sodium hydroxide solution are added dropwise within approx. 5 minutes—the pH value is adjusted to a range from 9.5 to 11.0. The mixture is then stirred for 0.5 h at 45° C. After phase separation, the lower aqueous phase is drained off and the organic phase is washed three times with completely deionised water, the washing water, as the heavier phase, in each case being drained off from beneath. The organic phase is then cooled to room temperature while being stirred, the product crystallising out during this operation. After at least 4 hours' crystallisation time, the product is removed by vacuum filtration. After NMR analysis for the content of phenol, isobutanol and tetraphenylphosphonium phenolate, the filtrate is returned to the reaction. The crystalline residue is rewashed with 2-propanol and then dried under a water-jet vacuum at 100° C.

The results are shown in Table 1.

TABLE 1

|  | Comparative Example 1 | Example 1 |
|---|---|---|
| Na [ppm] | 0.7 | <0.5 |
| Br [ppm] | 0.7 | 0.01 |
| Colour | light grey | colourless |

Examples of Use

B1) 114.15 g (0.500 mol) of bisphenol A and 113.54 (0.530 mol) of diphenyl carbonate are weighed out into a 500 ml three-necked flask equipped with a stirrer, internal thermometer and Vigreux column (30 cm, mirrored) with bridge. Atmospheric oxygen is removed from the apparatus by applying a vacuum and flushing with nitrogen (3 times) and the mixture heated to 150° C. 0.0173 g ($4\times10^{-3}$ mol %) of tetraphenylphosphonium phenolate (TPP-P) produced according to Example 1, relative to bisphenol A, are then added as a 3% phenolic solution and the resultant phenol removed by distillation at 100 mbar. The temperature is simultaneously raised to up to 250° C. The vacuum is then improved stepwise to 1 mbar and the temperature raised to 260° C. The temperature is then raised to 280° C. and the mixture stirred for 1.5 hours at 0.1 mbar. A light-coloured, solvent-free polycarbonate is obtained having a relative solution viscosity of 1.250 (dichloromethane, 25° C., 5 g/l).

The content of branching agent of the formula (VII) in the resultant polycarbonate is 25 ppm. The phenolic OH value of the polycarbonate is 70 ppm.

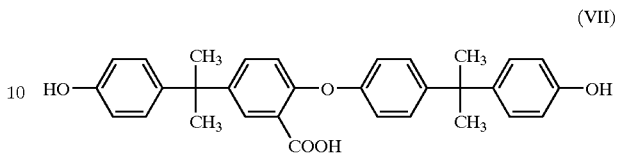
(VII)

B2) As Example B1), except that the temperature is raised from 260° C. to 300° C. and the mixture is stirred for 1.5 hours at 0.1 mbar. A light-coloured, solvent-free polycarbonate having a relative solution viscosity of 1.300 (dichloromethane, 25° C., 5 g/l) is obtained. The content of branching agent of the formula (VII) in the resultant polycarbonate is 18 ppm. The phenolic OH value of the polycarbonate is 55 ppm.

What is claimed is:

1. Process for the production of phosphonium phenolates by reacting phosphonium halides and phenols in an aqueous alkaline solution, characterised in that the phosphonium phenolate produced is separated from the synthesis mixture by crystallisation.

2. Process according to claim 1, characterised in that the reaction is performed at temperatures of 0 to 55° C.

3. Process according to claim 1, characterised in that the reaction is performed at molar ratios of phenol to phosphonium halide of 2:1 to 10:1.

4. Process according to claim 1, characterised in that the reaction is performed at pH values of 9.5 to 11.

5. Process according to claim 1, characterised in that the reaction is performed in the presence of alcohols in quantities of 66 wt. % to 125 wt. %.

6. Process according to claim 1, characterised in that crystallisation proceeds from an alcoholic solution.

7. Process according to claim 6, characterised in that the alcohol used is isobutanol.

8. Process according to claim 1, characterised in that the organic phase used is continuously recirculated.

9. Phosphonium phenolates obtained according to the process defined in claim 1.

10. Phosphonium phenolates having a halide content of no more than 0.1 wt. %.

11. A method of using the phosphonium phenolate of claim 9 comprising catalyzing a transesterification reaction.

12. The method of claim 11 wherein transesterification is for the production of polycarbonate.

* * * * *